United States Patent [19]

Blackburn et al.

[11] Patent Number: 4,980,163

[45] Date of Patent: Dec. 25, 1990

[54] NOVEL BACTERIOCIN COMPOSITIONS FOR USE AS ENHANCED BROAD RANGE BACTERICIDES AND METHODS OF PREVENTING AND TREATING MICROBIAL INFECTION

[75] Inventors: Peter Blackburn; Sara-Ann Gusik; June Polak; Stephen D. Rubino, all of New York, N.Y.

[73] Assignee: Public Health Research Institute of the City of New York, New York, N.Y.

[21] Appl. No.: 317,627

[22] Filed: Mar. 1, 1989

[51] Int. Cl.$^5$ .................... A61K 37/54; A61K 37/02
[52] U.S. Cl. ................. 434/94.63; 424/115; 514/2; 514/12
[58] Field of Search ............... 435/172.3; 514/2, 12; 424/115, 94.63

[56] References Cited

U.S. PATENT DOCUMENTS

| | | | |
|---|---|---|---|
| 2,744,827 | 5/1956 | Mattick et al. | 426/36 |
| 3,579,354 | 5/1971 | Kasik et al. | 426/36 |
| 3,899,594 | 8/1975 | Nickerson et al. | 426/9 |
| 3,988,307 | 10/1976 | Gross | 530/334 |
| 4,158,607 | 6/1979 | Kalinowski et al. | 435/221 |
| 4,318,928 | 3/1982 | Sing | 426/38 |
| 4,477,471 | 10/1984 | Gonzalez | 426/43 |
| 4,485,029 | 11/1984 | Kato et al. | 252/106 |
| 4,584,199 | 4/1986 | Taylor | 426/36 |
| 4,597,972 | 7/1986 | Taylor | 426/36 |
| 4,716,115 | 12/1987 | Gonzalez et al. | 435/172.3 |

OTHER PUBLICATIONS

Craven et al., Am. J. Vet. Res., vol. 44, No. 4, Apnl., 1983, pp. 709–712.
Hurst Advances in Applied Microbiology, 27:85–123.
Chemical Abstracts, vol. 77 (1972), p. 14, vol. 82 (1975) p. 94, vol. 86 (1977), vol. 89 (1978) pp. 64–65.
Reisinger et al., Arch. Microbiol., vol. 127, pp. 187–193 (1980).
Morris et al., J. Biol Chem., vol. 259, pp. 13590-4 (1984).
Ruhr et al., Antimicrob. Agents Chemother, vol. 27, pp. 841–845 (1985).
Tsai et al., Appl. Environ. Microbiol., vol. 53, pp. 352–357 (1987).
Claypool et al., Journal of Dairy Science.
Cowell et al., J. Appl. Bact. 34 (4), 787–791 (1971).
Johnson et al., J. Appl. Bact. 45 (1978), pp. 99–109.
"Focus on Nisin", Food Manufacture, Mar. 1987, pp. 63–64.
"A Natural Preservative" Food Eng. Int'l., May 1987, pp. 37–38.
Zygmunt et al., "Lysostaphin: Model for a Specfic Enzymatic Approach to Infectious Disease", Progress in Drug Research 16, 1972, pp. 309–333.
Weber et al., "Quaternary Ammonium Compounds," Soap & Sanitary Chemicals, Sep. 1948, pp. 137–142.

Primary Examiner—Howard E. Schain
Assistant Examiner—Choon Koh
Attorney, Agent, or Firm—White & Case

[57] ABSTRACT

Broad range bacteriocin compositions are provided. The compositions can be dissolved or suspended in a suitable solvent or matrix and are more active towards a broader range of bacteria than are any of the component parts. The dissolved or suspended compositions constitute enhanced broad range bactericides. The compositions include lysostaphin and a lanthionine containing peptide bacteriocin; lysostaphin, a lanthionine containing peptide bacteriocin and a chelating agent; and lysostaphin, a lanthionine containing peptide, a chelating agent and a surfactant. Each component is present in the enhanced broad range bactericide in sufficient amount such that the bactericide is more effective against staphylococci than is lysostaphin alone and is more effective at treating and preventing a broad range of microbial infections. Methods of treating bacterial infections using said compositions and bactericides are provided.

24 Claims, No Drawings

NOVEL BACTERIOCIN COMPOSITIONS FOR USE AS ENHANCED BROAD RANGE BACTERICIDES AND METHODS OF PREVENTING AND TREATING MICROBIAL INFECTION

BACKGROUND OF THE INVENTION

This application relates to bacteriocin compositions for use as enhanced broad range bactericides and methods of preventing and treating microbial infection.

Bacteriocins such as lysostaphin and nisin are proteins produced by bacteria that inhibit the growth of and sometimes kill bacteria closely related to the species of their origin. Lysostaphin is a bacteriocin that lyses and kills practically all known species of Staphylococcus, but is inactive against bacteria of other genera. Lysostaphin, isolated from culture filtrates of *Staphylococcus simulans* (NRRL B-2628) grown according to published references, is an endopeptidase which cleaves the polyglycine cross-links of the peptidoglycan found in the cell walls of Staphylococcus. Cultures of *S. simulans* grown under conditions which induce the production of lysostaphin are immune to the bacteriocin while the same cultures grown under conditions whereby lysostaphin is not produced are sensitive to the bacteriocin.

Lysostaphin is a naturally occurring bacteriocin secreted by a single known strain of *S. simulans* originally isolated and named *Staphylococcus staphylolyticus* by Schindler and Schuhardt. The production of lysostaphin by *S. staphylolyticus* has been described previously in U.S. Pat. No. 3,278,378 issued Oct. 11, 1966 and in *Proceedings of the National Academy of Sciences*, 51:414–421 (1964). The single organism *S. staphylolyticus* (NRRL B-2628) which produced lysostaphin was recently identified as a biovar of *S. simulans* by Sloan et al., *Int. J. System. Bacteriol.*, 32:170–174 (1982). Since the name *S. staphylolyticus* is not on the Approved List of Bacterial Names, the organism producing lysostaphin has been redesignated as *S. simulans*.

Previously it was shown that the action of lysostaphin can be potentiated by penicillin and other antibiotics. See copending U.S. application No. 188,183 to Blackburn et al. filed Apr. 28, 1988.

Nisan, although sometimes referred to as a peptide antibiotic is more properly referred to as a bacteriocin. Nisin is produced in nature by various strains of the bacterium *Streptococcus lactis*. It is a food preservative used to inhibit the outgrowth of spores of certain species of Gram positive bacilli, including those arising from strains of Clostridium known to be responsible for Botulism food poisoning. A summary of nisin's properties appears in Hurst, *Advances in Applied Microbiology*, 27:85–123 (1981). The publication describes what is generally known about nisin. Nisin, produced by *Streptococcus lactis*, is commercially available as an impure preparation, Nisaplin TM , (Aplin & Barret Ltd., Dorset, England)

Nisin belongs to the class of peptides containing lanthionine. Also included in that class are subtilin, epidermin, cinnamycin, duramycin, ancovenin, and Pep 5. These bacteriocin peptides are each produced by different microorganisms. However, subtilin obtained from certain cultures of *B. subtilis*, and epidermin obtained from certain cultures of *Staphylococcus epidermidis*, have molecular structures very similar to that of nisin, Hurst, pp. 85–86; and Schnell et al. *Nature* 333:276–278. Structurally similar, lanthionine containing peptide bacteriocins are believed to be effective in place of nisin in the present invention.

Nisin has been applied effectively as a preservative in processed cheese, and dairy products. The use of nisin in processed cheese products has been the subject of recent patents. See U.S. Pat. Nos. 4,584,199 and 4,597,972. The use of nisin to inhibit the outgrowth of certain Gram positive bacterial spores has been well documented. See Taylor, U.S. Pat. No. 5,584,199, and Taylor, U.S. Pat. No. 4,597,972, Tsai and Sandin, "Conjugal Transfer of Nisin Plasmid Genes from *Streptococcus lactis* 7962 to *Leuconostoc dextranicum* 181", *Applied and Environmental Microbiology*, p. 352 (1987); "A Natural Preservative", *Food Engineering International*, pp. 37-38 (1987); "Focus on Nisin", *Food Manufacture*, p. 63 (1987). Nisin is sometimes found naturally-occurring in low concentration in milk and cheese, and is believed to be completely non-toxic and non-allergenic to humans. Nisin has recently been recognized as safe by the FDA as a direct food ingredient in pasteurized cheese spread, pasteurized processed cheese spread and pasteurized or pasteurized processed cheese spread with fruits, vegetables, or meats. As nisin is proteinaceous, any residues in ingested foods are quickly degraded by digestive enzymes.

The general acceptance of nisin as a food preservative has been limited by the teaching that, as a bacteriocin, the activity of nisin was restricted to include only those Gram positive bacteria closely related to the bacterial species of its origin. Furthermore, nisin has not previously been shown to have bactericidal activity towards Gram negative bacteria. Since food contamination and spoilage result from a diversity of Gram positive and Gram negative bacteria, it is not surprising, therefore, that nisin has received only limited acceptance as a food preservative. Moreover, because of the heretofore restricted activity of nisin as a bacteriocin, its uses as such outside of the food area have not been indicated.

It has recently been demonstrated that a composition comprising nisin and non-bactericidal agents such as chelating agents and surfactants has bactericidal activity towards a wide range of Gram negative bacterial species and enhanced activity towards a broad range of Gram positive bacterial species. For instance Gram negative bacteria shown to be sensitive to the enhanced bactericide are *Salmonella typhimirium, Escherichia coli, Klebsiella pneumoniae, Pseudomonas aeruginosa, Bacterioides gingivalis* and *Actinobacillus actinomycetescomitans*. Gram positive bacteria shown to be sensitive to the enhanced bactericides are *Staphylococcus aureus, Streptococcus mutans, Listeria monocytogenes, Streptococcus agalactiae* and coryneform bacteria. See copending Blackburn et al., U.S. patent application entitled Nisin Compositions For Use as Enhanced, Broad Range Bactericides which is a continuation-in-part of U.S. patent application Ser. No. 209,861 filed June 22, 1988 which is hereby incorporated herein by reference.

SUMMARY OF THE INVENTION

It has now been found that the activity of bacteriocins such as lysostaphin and nisin can be surprisingly enhanced and the overall range and speed of their activity can be increased by combining the two bacteriocins. The properties of the novel bacteriocin compositions containing lysostaphin and nisin should also be further enhanced by the addition of chelating agents and/or surfactants which enhance and broaden the range of nisin and lysostaphin activity.

All the novel bacteriocin compositions of this invention comprise lysostaphin and nisin (herein "composition"). The bacteriocin composition becomes an enhanced broad range bactericide (hereinafter "bactericide") on being dissolved or suspended in a suitable carrier for example a solvent or suitable liquid, solid, or colloidal matrix. The novel bactericides contain lysostaphin in an amount sufficient to be effective as a bactericide towards Staphylococcus, and nisin is present in an amount sufficient to enhance the bactericidal effect of lysostaphin toward Staphylococci. Other compositions comprise lysostaphin, nisin, and a chelating agent and may also contain a surfactant. This composition in a carrier yields a novel bactericide wherein the lysostaphin and nisin are present in the same concentration range as in the lysostaphin/nisin composition and the chelating agent is present in an amount sufficient to enhance the bactericidal effect of nisin against both Gram positive and Gram negative bacteria. A still further composition comprises lysostaphin, nisin, and a surfactant. This composition in a carrier yields a novel bactericide wherein the surfactant is present in an amount sufficient to enhance the bactericidal effect of nisin and lysostaphin against Gram positive bacteria.

The compositions can be used directly or in carriers for treatment and prevention of bacterial contamination and infection by dissolving the composition in a suitable solvent or suspending in a suitable matrix and applying it to an affected area or by adding it to another composition to combat and prevent infection.

Most chemical disinfectants are too corrosive or otherwise too toxic to be used in foods and many medical applications, the majority of antibiotics act too slowly to be useful as disinfectants, and are not permitted in foods because of the risk of acquired antibiotic resistance that would attend such use. The novel bactericides are non-corrosive, non-toxic, suitable for use in foods and on open wounds, effective against antibiotic resistant bacteria and act rapidly against dividing or non-dividing bacteria, so as to be useful also as a disinfectant.

The compositions or the bactericides can be incorporated into ointments or coatings for the treatment of infections, wound dressings or surgical implants and other medications such as nasal instillations, oral rinses, disinfectant scrubs, wipes or lotions. The bactericides can be used for cleaning medical instruments and the like and in circumstances where environmental disinfection is desired but where chemical germicidals are precluded because of the risks of corrosive or otherwise toxic residues. The broad range bactericides are particularly suited for food related uses such as treatment of meat, especially poultry, eggs, cheese and fish or food packaging and handling equipment, and for the control and prevention of contamination of raw ingredients, processed foods and beverages by bacterial pathogens and other microbial spoilage organisms.

Unlike the activity of most broad spectrum germicidals which is compromised by the presence of complex organic matter, the bacteriocin compositions and bactericides of the present invention are effective in the presence of organic matter, such as milk or serum.

DETAILED DESCRIPTION OF INVENTION

The compositions of the claimed invention comprise lysostaphin and nisin, lysostaphin, nisin and a chelating agent, or lysostaphin, nisin, a chelating agent and a surfactant. To provide enhanced broad range bactericides, the compositions are dissolved in a suitable solvent or suspended in a suitable matrix. Compositions comprising lysostaphin, nisin, a chelating agent and/or a surfactant, dissolved in a suitable carrier for example an aqueous solvent or buffer or suspended in a suitable matrix, are believed to have broad range rapid bactericidal activity against both Gram positive and Gram negative bacteria.

Preferably the composition is dissolved in a liquid carrier or suspended in a liquid, colloidal or polymeric matrix such that lysostaphin is present in the bactericide in the range of 0.1 to 100 μg/ml and is enhanced by the presence of the bacteriocin nisin in the range of 0.1 to 300 μg/ml and the resulting bactericide is significantly more bactericidal towards Staphylococcus than lysostaphin alone. The total bactericidal activity of such a novel bactericide is believed to be further potentiated and effective against a broader range of both Gram negative and Gram positive bacterial species when the nisin in the bactericide is enhanced by a chelating agent as taught by copending application to Blackburn et al. entitled Nisin Compositions For Use as Enhanced, Broad Range Bactericides. The combination of lysostaphin, nisin and a chelating agent should also attain further broad range bactericidal activity by the addition of a surfactant as also taught by the Blackburn et al. application.

For example nisin is activated and enhanced toward a broad range of Gram positive bacteria by a chelating agent such as EDTA in the range of 0.1 to 20.0 mM. In the presence of EDTA, nisin has bactericidal activity against Gram negative organisms and its activity against Gram positive bacteria is enhanced and active over a wider pH range and towards a broader range of Gram positive bacteria. In addition the presence of a surfactant in the range of 0.01% to 1.0% in the bactericide improves the effectiveness of the nisin towards Gram positive bacteria. Suitable nonionic surfactants include, but are not limited to polyoxyalkylphenols (e.g. Triton X-100), polyoxyalkylsorbitans (e.g. Tweens), and glycerides (e.g. monolaurin and dioleates). Suitable ionic surfactants include, but are not limited to emulsifiers, fatty acids, quaternary compounds and anionic surfactants (e.g. sodium dodecyl sulphate) and amphoteric surfactants, for example, cocamidopropyl betaine.

Suitable carriers for the bactericides of the present invention include but are not limited to generally recognized aqueous buffers. Suitable matrices for suspension of the novel compositions of the present invention include but are not limited to organic solvents, colloidal suspension and polymers compatable with the bactericide.

Lysostaphin used in the invention can be produced by fermentation techniques wherein *S. simulans* is grown in liquid culture. Such fermentation techniques are described in U.S. Pat. No. 3,278,378 and in *Proceedings of the National Academy of Sciences*, 51:414–421 (1964). Various improvements in the production of lysostaphin by fermentation techniques have also been made as documented in U.S. Pat. Nos. 3,398,056, and 3,594,284. The latter two references disclose improvements in culture medium and inoculation techniques whereby the production of lysostaphin by fermentation can be accelerated and improved.

In addition, lysostaphin can be produced by recombinant microorganisms, including strains of *Escherichia* coli, Bacillus subtilus, and Bacillus sphaericus. A method for obtaining lysostaphin from microorganisms transformed by recombinant plasmids encoding the gene for lysostaphin is fully disclosed in U.S. patent application No. 034,464, which is a continuation-in-part of U.S. patent application No. 852,407. Both applications are incorporated herein by reference. Preferably, the lysostaphin is obtained from *B. sphaericus* strain 00, containing a recombinant plasmid which directs the synthesis of lysostaphin. This provides for production of high levels of lysostaphin substantially free from staphylococcal immunogenic contaminants and facile lysostaphin purification since the lysostaphin accumulates directly in the growth medium. *B. sphaericus* transformants containing plasmids pBC16-IL or pROJ6649-IL have been found to be particularly suited for this purpose, although other strains are also useful as a source of lysostaphin. These plasmids are fully described in the above-mentioned copending applications.

Produced by *S. simulans* during exponential growth, lysostaphin is first secreted as an inactive precursor that is processed extracellularly to the mature active bacteriocin by a protease produced in the stationary growth phase. In contrast to the natural production of lysostaphin, lysostaphin produced by a recombinant strain of *B. sphaericus* as described in U.S. patent application No. 034,464, accumulates extracellularly as the mature active protein during the exponential growth phase.

Nisin can be obtained commercially as an impure preparation, Nisaplin TM from Aplin & Barrett, Ltd., Dorset, England, and can be obtained by isolating naturally-occurring nisin from cultures of *Streptococcus lactis* and then concentrating the nisin by known methods. There are also reported methods for producing nisin using altered strains of Streptococcus. See Gonzalez, et al. U.S. Pat. No. 4,716,115 issued Dec. 29, 1987. It should also be possible to produce nisin by recombinant DNA. Nisin is a member of the family of lanthionine containing bacteriocins. It is believed that, due to the structural similarity, other lanthionine containing bacteriocins will be equally as effective as nisin in combination with lysostaphin.

The following non-limiting examples will further illustrate the invention and demonstrate the effectiveness of the new enhanced broad range bactericides. It is believed that since the degree and range of nisin activity are also enhanced by chelating agents, the compositions of lysostaphin, nisin and a chelating agent will also yield novel bactericides with enhanced bactericidal activity compared to compositions of lysostaphin and nisin alone.

All tests in the following examples were performed at 37° C. The efficacy of the enhanced broad range bactericides was determined by assaying bactericidal activity as measured by the percent bacterial survival after treatment with the bactericide. Generally, after incubation of a $10^7$ cell per ml suspension of target species with the novel bactericide for specified lengths of time, bacteria were collected by centrifugation for 2 minutes. The bacterial pellet was washed free of the bactericide with a rescue buffer, termed herein Phage buffer (50 mM Tris-HCl buffer pH 7.8, 1 mM $MgSO_4$, 4 mM $CaCl_2$, 0.1M NaCl, and 0.1% gelatin), resuspended and serially diluted into Phage buffer, and 100 μl of the suspended bacteria were spread on nutrient agar plates. Surviving bacteria were determined by scoring colony forming units (CFU) after incubation for 24–48 hours at 37° C. An effective bactericide according to this invention is one which allows less than 0.1% of the initial viable count of the bacteria to survive.

EXAMPLE 1

Lysostaphin and Nisin

*Staphylococcus aureus* cells were suspended and incubated in milk at 37° C. for 2 hours with various concentrations of lysostaphin, nisin, or a combination of lysostaphin and nisin in the milk. The bactericidal efficacy of the bactericides was estimated by determining the percent survival of bacteria as described above. The results of such an experiment are given in Table 1.

TABLE 1

Bactericidal Activity of Lysostaphin, Nisin, and Their Combinations Towards *Stachylococcus aureus*

| Lysostaphin μg/ml | Nisin μg/ml | | | | | |
|---|---|---|---|---|---|---|
| | 0 | 0.2 | 0.5 | 1.0 | 2.0 | 4.0 |
| | % survival 2 hr[a] | | | | | |
| 0 | 100 | 45 | 33 | 9 | 2.5 | 0.5 |
| | | | | | 0.5 | |
| 0.1 | 43 | 0.7 | 2.6 | 0.15 | 0.04 | 0.004 |
| | 5.6 | | | | $<10^{-3}$ | |
| 1.0 | $<10^{-3}$ | $<10^{-4}$ | — | — | $<10^{-4}$ | — |

[a]Initial viable counts: $5 \times 10^7$ cfu/ml.

Nisin alone in milk has little practical bactericidal activity towards Staphylococci. Lysostaphin alone in milk is bactericidal towards *S. aureus* and can produce more than a five log reduction in viable cells at a concentration of 1.0 μg/ml. Lysostaphin, when combined with nisin in the milk, provides a composition which is a novel bactericide whereby the bactericidal activity of the bactericide is significantly and surprisingly superior to that of either bacteriocin alone and is more active than their anticipated additive effects. This is best illustrated at a limiting lysostaphin concentration (0.1 μg/ml) shown in Table 1. Thus, when the application of lysostaphin is limited by its available activity, a bacteriocin composition comprising lysostaphin with nisin in a suitable carrier such as milk in this example can be expected to provide an enhanced broad range bactericide.

EXAMPLE 2

Lysostaphin+Nisin+EDTA+Surfactant

The data in Table 2 illustrate the novel bactericide potency of a composition comprising lysostaphin, nisin, EDTA, and monoglyceride surfactant towards *S. aureus* and *S. algalactiae* in milk, a complex food medium. Previously, it was shown that low concentrations of EDTA potentiate the activity of nisin while higher concentrations of EDTA inhibited the activity of nisin, see the copending application to Blackburn, et al. In milk, higher concentrations of EDTA are less inhibitory to the bactericidal activity of the bacteriocin composition.

TABLE 2

Bactericidal Activity of Lysostaphin, Nisin, EDTA, and Monoglyceride in milk at 37° C. towards *Staphylococcus aureus* and *Streptococcus agalactiae*

| Species | 0.23 L 1.0 N 0.1% ML | 0.1 L 1.0 N 1.0% ML | Control[c] |
|---|---|---|---|
| | % Survival 2 hr | | |
| *S. agalactiae*[b] (McDonald) | $0.0001^E$ | $0.0007^E$ | 100 |
| *S. aureus*[a] | $0.004^E$ | $0.002^E$ | 100 |

TABLE 2-continued

Bactericidal Activity of Lysostaphin, Nisin,
EDTA, and Monoglyceride in milk at 37° C. towards
Staphylococcus aureus and Streptococcus agalactiae

| Species | 0.23 L<br>1.0 N<br>0.1% ML | 0.1 L<br>1.0 N<br>1.0% ML | Control[c] |
|---|---|---|---|
| (Newbould) | | | |

N = Nisin μg/ml; L = Lysostaphin μg/ml; ML = monolaurin
E = contained 50 mM EDTA
a = S. aureus initial viable count: $8.1 \times 10^7$ cells/ml
b = S. agalactiae initial viable count: $6.6 \times 10^7$ cells/ml
c = no bacteriocin or monoglyceride

We claim:

1. A composition comprising lysostaphin and a lanthionine containing bacteriocin.

2. The composition as defined in claim 1 wherein the lanthionine containing bacteriocin is selected from the group consisting of nisin, subtilin, epidermin, cinnamycin, duramycin, ancovenin and Pep 5.

3. A composition as defined in claim 1 additionally comprising a chelating agent.

4. A composition as defined in claim 3 comprising a surfactant.

5. The composition as defined in claim 3 wherein the chelating agent is selected from the group consisting of alkyldiamine tetraacetates, CaEDTA, Na₂CaEDTA, EGTA and citrate.

6. The composition as defined in claim 5 wherein the alkyldiamine tetraacetate is EDTA.

7. The composition as defined in claim 4 or 23 wherein the surfactant is selected from the group consisting of Tritons, Tweens, glycerides, emulsifiers, fatty acids, quaternary compounds, amphoteric and anionic surfactants.

8. An enhanced broad range bactericide comprising a carrier, lysostaphin and a lanthionine containing bacteriocin.

9. The enhanced broad range bactericide as defined in claim 8 wherein the lanthionine containing bacteriocin is selected from the group consisting of nisin, subtilin, epidermin, cinnamycin, duramycin, ancovenin and Pep 5.

10. An enhanced broad range bactericide as defined in claim 8 comprising a chelating agent.

11. An enhanced broad range bactericide as defined in claim 8 comprising a surfactant.

12. The enhanced broad range bactericide as defined in claim 8 wherein the lysostaphin and the lanthionine containing bacteriocin are present in sufficient quantities such that the bactericide has enhanced activity against staphylococci and Gram positive bacteria.

13. The enhanced broad range bactericide as defined in claim 10 wherein the lysostaphin, the lanthionine containing bacteriocin and the chelating agent are present in quantities such that the bactericide has enhanced activity against staphylococci and against at least one of the bacteria from the group consisting of Gram negative and Gram positive bacteria.

14. The enhanced broad range bactericide as defined in claim 11 or 24 wherein the surfactant is present in an amount sufficient such that bactericide has enhanced activity against staphylococci and against at least one of the group consisting of Gram negative and Gram positive bacteria.

15. The enhanced broad range bactericide as defined in claim 10 wherein the chelating agent is selected from the group consisting of alkyldiamine tetraacetates, EGTA and citrate.

16. The enhanced broad range bactericide as defined in claim 15 wherein the alkyldiamine tetraacetate is EDTA.

17. The enhanced broad range bactericide as defined in claim 11 wherein the surfactant is selected from the group consisting of Tritons, Tweens, glycerides, fatty acids, emulsifiers, quaternary compounds, amphoteric and anionic surfactants.

18. The enhanced broad range bactericide as defined in claim 13 wherein the Gram negative bacterial target is selected from the group consisting of Salmonella typhimurium, Escherichia coli, Klebsiella pneumoniae, Pseudomonas aeruginosa, Bacterioides gingivalis and Actinobacillus actinomycetescomitans.

19. The enhanced broad range bactericide as defined in claim 13 wherein the Gram positive bacterial target is selected from the group consisting of spore forming bacilli, Staphylococcus aureus, Streptococcus mutans, Listeria monocytogenes, Streptococcus agalactiae, and cornyeform bacteria.

20. The enhanced broad range bactericide as defined in claim 9 wherein the effective concentration of lysostaphin is between about 0.1 to 100 μg/ml and the concentration of the nisin is between about 0.1 to 300 μg/ml.

21. The enhanced broad range bactericide as defined in claim 10 wherein the concentration of lysostaphin is between about 0.1 to 100 μg/ml, the concentration of the lanthionine containing bacteriocin is between about 0.1 to 300 μg/ml and the concentration of chelating agent is between about 0.1 mM and 20 mM.

22. The enhanced broad range bactericide as defined in claim 11 wherein the concentration of surfactant is between about 0.01% and 1.0% of the final volume.

23. A composition as defined in claim 1 comprising a surfactant.

24. An enhanced broad range bactericide as defined in claim 10 comprising a surfactant.

* * * * *